United States Patent [19]
Doorakian et al.

[11] 4,093,650
[45] June 6, 1978

[54] PROCESS FOR PREPARING TRIHYDROCARBYL (2,5-DIHYDROXYPHENYL) PHOSPHONIUM SALTS

[75] Inventors: George A. Doorakian, Bedford; Lawrence G. Duquette, Maynard, both of Mass.

[73] Assignee: The Dow Chemical Company, Midland, Mich.

[21] Appl. No.: 679,617

[22] Filed: Apr. 23, 1976

[51] Int. Cl.$^2$ ............................................. C07C 53/08
[52] U.S. Cl. .......................... 260/539 A; 260/526 N; 260/606.5 F; 260/606.5 N
[58] Field of Search ................ 260/606.5 P, 606.5 N, 260/526 N, 539 A, 541, 606.5 F

[56] References Cited

U.S. PATENT DOCUMENTS 2,862,970   12/1958   Thielen ........................... 260/606.5 F

OTHER PUBLICATIONS

Arshad et al., Pakistan J. Sci. Ind. Res. 12, 334–336 (1970) (Corresponding C.A. Article of record).
Ramirez et al., J.A.C.S. 78, 5614–5622 (1956).
Kosolapoff, Organic Phosphorus Compounds, Wiley–Interscience N.Y. vol. 2, pp. 197–198 (1972).
Grapon et al., Topics in Phosphorus Chemistry, Interscience Publ. N.Y., vol. 3, pp. 23–27 (1966).
Arshad et al., Tetrahedron Letters, vol. 22, pp. 2203–2211 (1966), Chemical Abstracts, U73, 65576u (1970).

*Primary Examiner*—Helen M. S. Sneed
*Attorney, Agent, or Firm*—L. Wayne White

[57] ABSTRACT

The title compounds are prepared by reacting (a) a trihydrocarbylphosphine, (b) p-benzoquinone, and (c) a protic acid in a liquid reaction medium comprising a lower alkanol of from 1 to 4 carbon atoms, a 1,2-alkylene glycol, dialkylene glycol or trialkylene glycol or a lower alkyl mono-ether of said glycols. The glycols are either ethylene glycol, propylene glycol, or the indicated oligomers thereof. Methanol is the solvent of choice. As an example, tri-n-butyl (2,5-dihydroxyphenyl)phosphonium chloroacetate was prepared in excellent yields by slowly adding tri-n-butylphosphine, precooled to about 0° C, to a vigorously stirred suspension of p-benzoquinone in a methanol solution of chloroacetic acid at a temperature of approximately −10° C. A precatalyzed epoxy resin was obtained by merely adding the methanol solution of the phosphonium chloroacetate to a liquid epoxy resin (e.g., the diglycidyl ether of bisphenol-A).

12 Claims, No Drawings

PROCESS FOR PREPARING TRIHYDROCARBYL (2,5-DIHYDROXYPHENYL) PHOSPHONIUM SALTS

BACKGROUND OF THE INVENTION

The tri-substituted (2,5-dihydrophenyl)phosphonium salts are latent catalysts for promoting the reaction between vicinal epoxides and phenols and/or carboxylic acids (or anhydrides). Pre-catalyzed epoxy resins are easily prepared using such catalysts. This utility and a full description of the salts is set forth in our co-pending application Ser. No. 481,599 filed June 21, 1974, the disclosure of which is incorporated herein by reference. This application is directed to a method of preparing one of the classes of compounds set forth in Ser. No. 481,599 which is represented by formula I

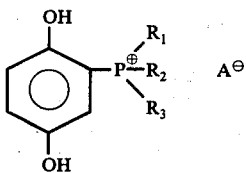

wherein $R_1$-$R_3$ are hydrocarbyl or inertly-substituted hydrocarbyl radicals, each of which independently has from 1 to about 20 carbon atoms, and $A^\ominus$ is a compatible neutralizing anion.

Such compounds were previously prepared by reacting the appropriate tri-substituted phosphine with p-benzoquinone in benzene solution. This method was described by Ramirez et al., J. Am. Chem. Soc., Vol. 78, 5614 (1956). In this technique, the phosphobetaine was first obtained as a solid precipitate which was isolated and subsequently converted to the corresponding phosphonium salt by reaction with an aqueous protic acid or a methanol/water solution of the acid.

SUMMARY OF THE INVENTION

We have discovered a new method of preparing tri-substituted (2,5-dihydroxyphenyl)phosphonium salts of formula I above. The new process comprises reacting by contacting (a) a phosphine of the formula $R_1R_2R_3P$, wherein $R_1$-$R_3$ have the aforesaid meanings, (b) p-benzoquinone, and (c) a protic acid of the formula $H^{\oplus}A^\ominus$, in a liquid reaction medium consisting essentially of a lower alkanol of from 1 to 4 carbon atoms, 1,2-ethylene glycol, 1,2-propylene glycol, diethylene or dipropylene glycol, triethylene or tripropylene glycol, or a lower alkyl ($C_1$-$C_4$) ether of said glycols, or a mixture thereof. The desired product is obtained as a solution in the liquid reaction medium and can be used as such in catalyzing the reaction of epoxides with phenols and/or carboxylic acids (or anhydrides). This is a substantial advantage because the isolation and purification steps normally necessitated in the Ramirez et al. process are thereby eliminated. Alternatively, of course, the desired product can be isolated and recovered from the reaction mixture by conventional techniques (e.g., by solvent extraction or by stripping off the solvent under reduced pressure, etc.).

DETAILED DESCRIPTION OF THE INVENTION

The solvents in the instant invention are lower alkanols of from 1 to 4 carbon atoms (e.g., methanol, ethanol, n-propanol, isopropanol, n-butanol, etc.), 1,2-ethylene glycol or 1,2-propylene glycol and dimers and trimers of the ethylene and propylene glycols, lower alkyl ($C_1$-$C_4$) ethers of said glycols (e.g., the methyl and butyl ether of diethylene glycol, etc.), and mixtures of such solvents. Methanol is the solvent of choice.

The reactants in the instant process are well known classes of compounds, essentially any member of which can be used in the instant process. The preferred phosphine reactants are tri-n-butylphosphine and triphenylphosphine with the tri-n-butylphosphine being the most preferred.

The anion $A^\ominus$ in the product may be predetermined by choosing the appropriate inorganic or organic protic acids which supply the requisite anion $A^\ominus$. Alternatively, the anion of any particular compound of formula I can be exchanged for another anion by conventional anion exchange techniques. Ser. No. 481,599 teaches that the non-nucleophilic anions (such as bisulfate, acetate, chloroacetate, diacetate, adipate, etc.) are preferred when the phosphonium salts are used in preparing pre-catalyzed epoxy resins. Ser. No. 481,599 also teaches that bromide and iodide anions are the preferred nucleophilic anions.

The reaction temperature may be varied to convenience but best results are achieved when the reaction temperature is maintained at a temperature of between the freezing point of the reaction mixture and about 60° C. Preferably, the reaction temperature is maintained between the freezing point of the reaction mixture and about 0° C, more preferably from about −40° C to about 0° C. The reaction rate is very high even at these rather low temperatures and the product yield is increased at the expense of reaction by-products.

The ratio of the reactants may be varied although best results are achieved when essentially stoichiometric quantities of the reactants are used. A slight excess of the phosphine reactant is advantageous to maximize conversion of the reactants to the desired product.

The order of addition is not absolutely critical but best results are achieved when the phosphine reactant is added to an efficiently blended reaction mixture of the p-benzoquinone and acid reactants in the liquid reaction medium.

EXPERIMENTAL

The following examples will further illustrate the invention.

EXAMPLES 1 - 6 PREPARATION OF TRI-N-BUTYL (2,5-DIHYDROXYPHENYL)PHOSPHONIUM SALTS

Neat tri-n-butylphosphine (106.4 g, 0.525 mole) at 0° C was added in increments to a vigorously stirred, pre-cooled (approximately −40° C to −20° C) suspension of p-benzoquinone (54.1 g, 0.50 mole) in a methanol solution containing 0.50 mole of the acid indicated in Table 1 below. The temperature of the reaction mixture was maintained at approximately −10° C during the addition of the phosphine reactant. After the addition of the phosphine was complete, the reaction mixture was observed for turbidity and, if turbid, the temperature was allowed to exotherm until a clear solution was obtained. Then, the temperature of the resulting solution was lowered to about −10° C for an additional half hour of vigorous stirring. The amount of methanol in each instance was selected such that the weight of the methanol was equal to the combined weight of the reactants.

TABLE 1

| Ex | $H^{\oplus}A^{\ominus}$ | Reaction Exotherm Allowed/Time | Product Yield (%) |
|---|---|---|---|
| 1 | $HBF_4$ (50% in $H_2O$) | 35° C/5 minutes | 97 |
| 2 | $H_3PO_4$ (85% in $H_2O$) | 25° C/5 minutes | 84 |
| 3 | HCl (37% in $H_2O$) | 30° C/5 minutes | 96 |
| 4 | $CH_2$=CHCOOH | 12° C/5 minutes | 81 |
| 5 | $ClCH_2COOH$ | −10° C/35 minutes | 96 |
| 6 | $CH_3COOH$ | −10° C/20 minutes | 89 |

The product yield in the above samples was determined by comparing the U.V. absorption of the methanol solution of the reaction product at $317_{nm}$ versus the U.V. absorption of a 50 weight percent of authentic sample in methanol ($\xi 317_{nm} = 4971.0$).

The desired products were obtained as a crystalline solid by evaporating the methanol solvent from the reaction products and triturating the residues with acetone. Elemental analyses on the crystalline solids so obtained were very close to the theoretical calculations.

Methanol solutions of reaction product from Examples 1-6 were easily blended with liquid epoxy resins (e.g., the diglycidyl ether of bisphenol-A). Substantially linear high molecular weight epoxy resins were obtained having epoxy values very close to theoretical when the epoxy resin/phosphonium salt mixtures were reacted with bisphenol-A at 160° C for 4-6 hours. Other phosphonium salts, as described above, can be similarly prepared and used.

We claim:

1. A process for preparing a compound of the formula

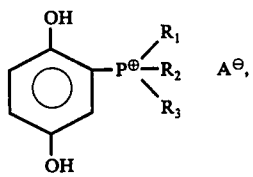

wherein:
$R_1$, $R_2$ and $R_3$ are each independently hydrocarbyl or inertly-substituted hydrocarbyl groups of from 1 to about 20 carbon atoms, and $A^{\ominus}$ is an inert neutralizing anion; said process comprising reacting by contacting in essentially stoichiometric amounts
(a) a phosphine of the formula $R_1R_2R_3P$, wherein $R_1$-$R_3$ have the aforesaid meanings,
(b) p-benzoquinone, and
(c) a protic acid of the formula $H^{\oplus}A^{\ominus}$,
wherein $A^{\ominus}$ has the aforesaid meaning in a liquid reaction medium consisting essentially of a lower alkanol of from 1 to 4 carbon atoms, 1,2-ethylene glycol, 1,2-propylene glycol, diethylene glycol, dipropylene glycol, triethylene glycol, tripropylene glycol, or a lower alkyl ($C_1$-$C_4$) ether of said glycols, or a mixture thereof.

2. The process defined by claim 1 wherein $R_1$-$R_3$ are each phenyl or n-butyl.

3. The process defined by claim 2 wherein $R_1$-$R_3$ are each n-butyl.

4. The process defined by claim 1 wherein said process is conducted at a reaction temperature of from the freezing point of the reaction mixture up to about 60° C.

5. The process defined by claim 4 wherein the reaction temperature is from the freezing point of the reaction mixture up to about 0° C.

6. The process defined by claim 5 wherein the reaction temperature is from about −40° C to about 0° C.

7. The process defined by claim 1 wherein (a) is added incrementally to an efficiently blended reaction mixture of (b) and (c) in said liquid reaction medium.

8. The process defined by claim 7 wherein $R_1$-$R_3$ are each n-butyl or phenyl; the reaction temperature is from about −40° C to about 0° C; and said liquid reaction medium is methanol.

9. The process defined by claim 8 wherein $R_1$-$R_3$ are each n-butyl and (c) is $HBF_4$, $H_3PO_4$, HCl, acrylic acid, chloroacetic acid or acetic acid.

10. The process defined by claim 9 wherein (c) is chloroacetic acid.

11. The process defined in claim 1 wherein $A^{\ominus}$ is bromide, iodide or a non-nucleophilic anion.

12. The process defined by claim 11 wherein said non-nucleophilic anion is bisulfate, acetate, diacetate, chloroacetate, trifluoroacetate, acrylate, or adipate.

* * * * *

UNITED STATES PATENT AND TRADEMARK OFFICE
CERTIFICATE OF CORRECTION

PATENT NO. : 4,093,650

DATED : June 6, 1978

INVENTOR(S) : George A. Doorakian and Lawrence G. Duquette

It is certified that error appears in the above-identified patent and that said Letters Patent are hereby corrected as shown below:

Column 1, line 51, delete "$H^{61}A^{\ominus}$," and insert -- $H^{\oplus}A^{\ominus}$, wherein $A^{\ominus}$ has the aforesaid meaning --.

Column 2, line 5, after the parenthesis delete the first period.

Signed and Sealed this

Seventh Day of November 1978

[SEAL]

Attest:

RUTH C. MASON
*Attesting Officer*

DONALD W. BANNER
*Commissioner of Patents and Trademarks*